(12) United States Patent
Alberto et al.

(10) Patent No.: US 8,961,924 B2
(45) Date of Patent: Feb. 24, 2015

(54) METAL COMPLEXES

(75) Inventors: Roger Alberto, Zurich (CH); Henrik Braband, Zurich (CH)

(73) Assignee: University of Zurich (CH)

( * ) Notice: Subject to any disclaimer, the term of this patent is extended or adjusted under 35 U.S.C. 154(b) by 530 days.

(21) Appl. No.: 12/921,794

(22) PCT Filed: Mar. 10, 2009

(86) PCT No.: PCT/GB2009/000650
§ 371 (c)(1),
(2), (4) Date: Sep. 10, 2010

(87) PCT Pub. No.: WO2009/112823
PCT Pub. Date: Sep. 17, 2009

(65) Prior Publication Data
US 2011/0065680 A1  Mar. 17, 2011

(30) Foreign Application Priority Data
Mar. 10, 2008 (GB) .................................. 0804406.7

(51) Int. Cl.
| | | |
|---|---|---|
| *A61K 51/00* | (2006.01) | |
| *A61M 36/14* | (2006.01) | |
| *A61K 51/04* | (2006.01) | |
| *C07F 13/00* | (2006.01) | |

(52) U.S. Cl.
CPC ........... *A61K 51/0482* (2013.01); *C07F 13/005* (2013.01)
USPC ........................................ 424/1.11; 424/1.65

(58) Field of Classification Search
USPC ...................................................... 424/1.11
See application file for complete search history.

(56) References Cited

U.S. PATENT DOCUMENTS

| | | | | |
|---|---|---|---|---|
| 4,272,503 | A | | 6/1981 | Camin et al. |
| 4,617,184 | A | * | 10/1986 | Tsolis et al. .................... 534/14 |
| 2002/0147316 | A1 | | 10/2002 | Pipes et al. |
| 2004/0042963 | A1 | | 3/2004 | Katti et al. |
| 2008/0025915 | A1 | | 1/2008 | Babich et al. |

FOREIGN PATENT DOCUMENTS

| | | | |
|---|---|---|---|
| EP | 0 386 873 | 9/1990 | |
| EP | 0953360 | 3/1999 | |
| EP | 1092723 | 4/2001 | |
| JP | 54-160305 | 4/1979 | |
| JP | 11-292797 | 10/1999 | |
| JP | 2001-114792 | 10/1999 | |
| JP | 2007-523902 | 9/2006 | |
| WO | WO 2005011738 A2 * | 2/2005 | ............. A61K 47/00 |
| WO | 2005079866 | 9/2005 | |

OTHER PUBLICATIONS

Anthony et al. (Inorg. Chem. 1992, 31, 1976-1978).*
Pinkerton et al. (J. Electroanalyt. Chem. Interfac. Electrochem. 1983, 158, 323-340).*
Mundwiler et al. (Bioconj. Chem. 2004, 15, 195-202).*
Banbery et al., "Communication the Syntheses of High Oxidation State Metal Complexes Containing the Tripodal Ligand . . . ", Polyhedron, 1990, 9(20), pp. 2549-2551.
Botha et al., "Chelation Processes to an Oxorhenium(V) Center by . . . ", Inorg. Chem., 1998, 37, pp. 1609-1615, XP 002539124.
Braband et al., "Technetium Complexes with Triazacyclononane", Inorg. Chem., 2006, 45, pp. 6589-6591, XP 002526207.
Gable et al., "Cycloreversion of Rhenium(V) Diolates Containing the . . . ", Organometallics, 1999, 18, pp. 173-179, XP 002539125.
Gable et al., "Cycloreversion of Rehnium(V) Diolates Containing the . . . ", Organometallics, 1999, 18, pp. 173-179, XP 002526208.
Gable et al., "Kinetic Isotope Effects in cycloreversion of Rhenium (V) Diolates", J. Am. Chem. Soc., 2002, 124, pp. 3970-3979, XP 002539126.
Gable et al., "Kinetics and Mechanism of Rhenium-Catalyzed O Atom Transfer from Epoxides", J. Am. Chem. Soc., 2003, 125, pp. 11018-11026, XP 002539127.
Gable et al., "Reaction of Strained-Ring Heterocycles with a Rhenium(V) Dioxo Complex", Organometallics, 2004, 23, pp. 5268-5274, XP 002539128.
Greenland et al., "Water-Soluble Phosphines for direct labeling of Peptides with Technetium . . . ", Bioconjugate chem., 2005, 16, pp. 939-948.
Herrmann et al., "Multiple Bonds between Transition Metals and Main-Group Elements . . . ", Inorganic Chemistry, 1995, 34(19), pp. 4701-4707, XP 002539123.
Joachim et al., "Synthese, charakterisierung und . . . ", Zeitschrift Fur Naturforschung, 48(2), 1993, pp. 227-229, XP 009120731.
Paulo et al., "Synthesis, characterization, and Study of the Redox Properties . . . ", Inorg. Chem., 1994, 33, pp. 4729-4737, XP 002539121.
Sugimoto et al., "A Series of Oxorhenium(V) complexes Containing Tridentate . . . ", chemistry Letters, 1997, 6, pp. 541-542, XP 009120730.
Suzuki et al., "Assessment of Macrocyclic Triamine Ligands As Synthons for . . . ", Inorg. Chem., 2008, 47, pp. 2593-2600, XP 002526211.
Thomas et al., "High oxidation state technetium and rhenium complexes of . . . ", Inorganica chimica Acta, 1991, 190, pp. 231-235, XP 002526212.
Tooyama et al., "high-Valent Technetium complexes with the . . . ", Inorg. Chem., 2008, 47, pp. 257-264, XP 002526209.
Vanbilloen et al., "Preparation, characterization and biological evaluation . . . ", J. Label. Compd. Radiopharm., 2005, 48, pp. 1003-1011, XP 002526210.

* cited by examiner

*Primary Examiner* — Michael G Hartley
*Assistant Examiner* — Melissa Perreira
(74) *Attorney, Agent, or Firm* — Mallinckrodt LLC (57) ABSTRACT

A method for synthesizing a complex having the formula: $[L_3MO_3]^n$ wherein $L^3$ represents a tridentate ligand, M represents a metal selected from Tc an Re, and n is a charge from −2 to +1, the method comprising: a) reaction of pertechnetate or perrhenate with a reducing agent and $L^3$, or b) reaction of pertechnetate or perrhenate with a Lewis acid and $L^3$, wherein the synthesis (a) or (b) is carried out in an aqueous medium.

12 Claims, 10 Drawing Sheets

METAL COMPLEXES

CROSS REFERENCE TO RELATED APPLICATIONS

This application is a national stage application of PCT/GB2009/000650, filed Mar. 10, 2009, which claims the benefit of G.B. Application No. 0804406.7, filed Mar. 10, 2008.

The present invention relates to metal complexes. In particular, though not exclusively, it relates to technetium complexes containing the $[TcO_3]^+$ core and rhenium complexes containing the $[ReO_3]^+$ core, particularly those in which the technetium is in the form of the Tc-99m isotope, and the rhenium is in the form of the Re-186 or Re-188 isotope.

The $[TcO_3]^+$ core represents probably the smallest moiety that exists in technetium chemistry and which can be stabilized by coligands. It would be highly desirable to find a convenient access to complexes comprising this simple core structure.

Braband and Abram (*Inorg. Chem.*, 2006, 45, 6589-6591) describe the preparation of a $[TcO_3]^+$-containing complex with the tridentate ligand triazacyclononane. The corresponding glycolato derivative is also disclosed as an intermediate in the preparation thereof. However, only ground state Tc-99 is used, and the starting Tc-containing material is not suitable for large-scale nuclear medicine applications. Thomas and Davison (*Inorg. Chim. Acta*, 1991, 190. 231-235) describe the preparation of tris-pyrazolylborate complexes containing the $[TcO_3]^+$ core. Again ground state Tc-99 was used in the form of a complex starting material. In addition, harsh conditions, involving the use of concentrated acid, are used in the synthesis; such conditions are not suitable for nuclear medicine applications. Banberry et al. (*Polyhedron*, 1990, 9, 2549-2551) also disclose complexes containing the $[TcO_3]^+$ core with ground state Tc-99. Again, harsh conditions (peracetic acid) are employed. Tooyama et al. (*Inorg. Chem.*, 2008, 47, 257-264) describe the preparation of $[TcO_3]^+$ and $[ReO_3]^+$ complexes with the ligands bis(3,5-dimethyl-1H-pyrazol-1-yl)acetate and 1,1,1-methanetriyltris(3,5-dimethyl-1H-pyrazole). The synthesis is conducted using strong Lewis acids as activating agents in non-aqueous media. Indeed, the activating agents used would not be compatible with aqueous media since they would react with the water.

Despite being a Tc-containing core of potential interest, no synthetic approaches to the preparation of $[^{99m}TcO_3]^+$ containing complexes have been described so far since $[^{99m}TcO_4]^-$ as such, the most convenient form of $^{99m}Tc$ for nuclear medicine applications and typically being contained in generator eluate, is generally regarded as being too unreactive and difficult to activate, particularly in water. Furthermore, the prior art approaches described above employ organic solvents for the synthesis of the core/complex, such solvents being incompatible with manufacturing-scale synthesis for nuclear medicine applications in humans or animals. Moreover, in the prior art complexes described above, the ligands used for complexation of the metal trioxide core do not bear targeting moieties, nor do they bear spacer or linker groups which are suitable for attachment of such targeting moieties. Accordingly, they are of limited use for in vivo radiopharmaceutical applications, where targeting of the metal to particular cells or tissues is frequently desired for imaging purposes.

In accordance with a first aspect of the present invention, there is provided a method for synthesizing a complex having the formula:

$$[L^3MO_3]^n$$

wherein $L^3$ represents a tridentate ligand, M represents a metal selected from Tc and Re, and n is a charge from −2 to +1, the method comprising:

a) reaction of pertechnetate or perrhenate with a reducing agent and $L^3$, or b) reaction of pertechnetate or perrhenate with a Lewis acid and $L^3$, wherein the synthesis (a) or (b) is carried out in an aqueous medium.

In certain embodiments, the method of the present invention comprises:

a) i) reaction of pertechnetate or perrhenate with a reducing agent; ii) coordination of $L^3$ with the resulting Tc or Re species, respectively; and iii) oxidation of the Tc or Re species to the (VII) oxidation state;

or b) i) reaction of pertechnetate or perrhenate with a Lewis acid; and ii) coordination of $L^3$ with the resulting Tc or Re species, respectively.

The synthetic methods of the present invention allow the preparation of complexes containing the $[TcO_3]^+$ or $[ReO_3]^+$ core directly from water/saline. This is significant since it allows the preparation of complexes containing the core directly from generator eluate. Since the resulting complexes contain Tc or Re in their highest oxidation states, they are not prone to subsequent oxidation, a problem which is particularly relevant for radiopharmaceuticals in lower oxidation states, such as +V. Preferred isotopes of Tc and Re for use in the method include $^{99m}Tc$ and $^{186}Re$ and $^{188}Re$. Given the relatively short half-life of the preferred isotope, $^{99m}Tc$ (around 6 hours), it will be apparent that the ability to prepare complexes useful for nuclear medicine applications directly from the eluate, without the need for multiple time-consuming processing steps, confers an important advantage. The properties of the complexes are also very important in this regard, e.g. their oxidation stability. The methods also avoid the use of potentially toxic solvents and reagents which would be incompatible with uses in nuclear medicine.

The method of synthesis of the present invention presents two possibilities for the preparation of complexes with the $[TcO_3]^+$ or $[ReO_3]^+$ core. According to the first possibility (a), reduction of pertechnetate to Tc(V) is undertaken by means of a reducing agent, which may be a Lewis base, with coordination of the reduced species with the ligand $L^3$, followed by subsequent oxidation to the $TcO_3$-containing complex. The oxidation step may be achieved using air (e.g. air in the reaction vessel). The same approach may be employed with perrhenate. According to the second possibility (b), pertechnetate or perrhenate should first be activated by reaction with an aqueous-compatible Lewis acid (for example by formation of an ester, a mixed anhydride or a similar structural unit) before ligand substitution or coordination takes place. Various activation strategies would be apparent to the skilled person, although the non-reducing, element group III, IV or V based Lewis acids may be mentioned. Neither of these strategies has been explored so far, or suggested, in the prior art.

As reducing Lewis bases for use in the method of synthesis of the present invention, phosphines may be mentioned. The reaction may be homogeneous, e.g. using a solution of phosphinic acid or a water-soluble phosphine or substituted phosphine, or may be heterogeneous, e.g. using an inorganic or organic polymer-bound phosphine or substituted phosphine. Polymeric (e.g. resin-based) reducing agents (such as phosphines) or activating Lewis acids have the advantage that they can easily be separated from the reaction products, e.g. by filtration. The polymeric support for the polymer-bound reducing agents or activating Lewis acids for use in accordance with the invention may be based on an inorganic or organic polymer, each of which may be presented in the form of beads. Polymeric reducing agents and Lewis acids are commercially available and may be based, for example, on an organic polymer, such as polystyrene, which may be in the form of beads. Examples of suitable inorganic polymeric supports include those based on silica. The polymeric supports may contain spacer groups (such as poly(alkylene glycol) chains) to which the reducing agents or activating Lewis acids are attached.

In certain embodiments, the phosphine is substituted, e.g. with alkyl (preferably $C_{1-5}$) or aryl groups which may themselves be further substituted. In particular, the phosphine may be phenyl substituted. Preferred phosphines include di- and triphenylphosphines. As a further embodiment, phosphines based on 3,3',3"-phosphinetripropanoic acid may be mentioned.

In alternative embodiments, the reducing agent used in synthesis (a) is selected from phosphites, sulphites, hypophosphites, and hydrides. Again, solid-phase, or inorganic or organic polymeric forms of such reducing agents may be preferred in certain embodiments.

In certain embodiments of the method of the present invention, $L^3$ and the reducing agent, or $L^3$ and the Lewis acid, may be presented simultaneously in the form of an adduct or conjugated form of these two components. Thus, it is possible to employ an adduct of the borohydride, borane, with a tridentate ligand such as triazacyclononane. It is also possible to employ an adduct of such a ligand with a phosphine (e.g. a triphenylphosphine), e.g. in the form of a phosphoylid (in the example of triazacyclononane, an aminophosphoylid).

The method of synthesis of the present invention may be carried out in saline. In particular, the method may be carried out in saline-based eluate from a Tc or Re generator.

In certain embodiments of the method of synthesis, $L^3$ represents a tridentate ligand bearing one or more functional groups suitable for facilitating the attachment of a targeting moiety, or bearing one or more linker groups capable of bearing such a functional group. The said functional groups may also, or alternatively, be useful for modifying the physicochemical properties of the resulting complex, or for facilitating the attachment of further moieties capable of modifying those properties. Such further moieties may include, for example, poly(alkylene glycol) groups or carbohydrates. As used herein, the term, 'functional group suitable for facilitating the attachment of a targeting moiety' includes functional groups suitable for facilitating the attachment of further moieties capable of modifying the physicochemical properties of the resulting complex.

The ability to modify $L^3$ with functional groups allows an increased degree of control over the physicochemical properties (and hence pharmacological behaviour) of the complexes. When the functional groups are suitable for reaction with corresponding groups on targeting moieties, they allow the conjugation of the complex and the targeting moiety. This allows targeting of the complex to particular biological sites. The conjugation of the targeting moiety to $L^3$ may be performed prior to or after the formation of the complex, but is preferably carried out before. The same applies in the case of conjugation of moieties capable of modifying the physicochemical properties of the resulting complexes.

When $L^3$ bears one or more linker groups, none of which bears a functional group suitable for the attachment of a targeting moiety, the linker groups may contain at least three carbon atoms.

$L^3$ usually contains at least three oxygen and/or nitrogen atoms which have lone pairs of electrons available for coordination with the Tc or Re atom of the $TcO_3/ReO_3$ core. In certain embodiments, $L^3$ contains 2 or 3 nitrogen atoms containing lone pairs of electrons. In particular, the nitrogen atoms of $L^3$ may form part of primary or secondary amino groups. In certain ligands $L^3$, the primary or secondary amino groups may be present on or as part of separate cyclic moieties which are connected by an intervening group or atom. Alternatively or in addition, two or more of the primary or secondary amino groups may be present on or as part of the same cyclic moiety. In particular embodiments, $L^3$ may be a triazacyclononane, a triaminocyclohexane, a trispyrazolylmethane, a bispyrazolylacetate, a trispyrazolylborate or a corresponding imidazolyl species. In such embodiments, or indeed in other embodiments in which $L^3$ contains nitrogen atoms, $L^3$ may be N-substituted with one or more functional groups which may be suitable for facilitating the attachment of a targeting moiety, or may be N-substituted with one or more linker groups capable of bearing such a functional group.

As linker groups suitable for use according to the present invention, the following may be mentioned: alkyl (e.g. $C_1$, $C_2$, $C_3$, $C_4$ or $C_5$ alkyl), alkenyl (e.g. $C_1$, $C_2$, $C_3$, $C_4$ or $C_5$ alkenyl), aryl (e.g. five- to nine-membered aromatic rings, such as five, six or seven membered rings), heteroaryl (e.g. five- to nine-membered rings including 1, 2 or 3 heteroatoms), cycloalkyl (e.g. five- to nine-membered non-aromatic rings, such as five, six or seven-membered rings), heterocycloalkyl (e.g. five- to nine-membered non-aromatic rings including 1, 2 or 3 heteroatoms), aralkyl (e.g. $C_1$, $C_2$, $C_3$, $C_4$ or $C_5$ alkyl, bearing e.g. one or more five- to nine-membered aromatic rings, such as five, six or seven membered rings), and alkaryl (e.g. one or more five- to nine-membered aromatic rings, such as five, six or seven-membered rings, bearing one or more e.g. $C_1$, $C_2$, $C_3$, $C_4$ or $C_5$ alkyl groups) groups, any of which linker groups may be further substituted with a functional group suitable for facilitating the attachment of a targeting moiety. Equally, $L^3$ may be substituted with one or more essentially non-reactive groups which are nevertheless capable of modifying the pharmacological behaviour of the complex. Such groups include short (e.g. $C_1$ or $C_2$) alkyl substituents, or aryl substituents containing no further functional groups, and are intended to be included, unless the context requires otherwise, within the definition of 'linker group'. Thus, in certain embodiments, such linker groups may act merely as substituents on $L^3$, rather than to link a functional group thereto.

The functional group suitable for facilitating the attachment of a targeting moiety may, in certain embodiments, be selected from hydroxyl, carboxyl, amino, amido, halogen, sulphonyl, alkylsulphonyl, arylsulphonyl, alkylsulphonylamido, arylsulphonylamido, thio, alkylthio, arylthio, phosphonyl, phosphate and cyano groups.

In a related second aspect, the present invention also provides a composition comprising an aqueous solution of a complex having the formula:

$$[L^3MO_3]^n$$

wherein $L^3$ represents a tridentate ligand, M represents a metal selected from Tc and Re, and n is a charge from −2 to +1, the composition being obtained or obtainable by a method according to the present invention as described above.

In accordance with a third aspect of the present invention, there is provided a complex having the formula:

$$[L^3MO_3]^n$$

wherein $L^3$ represents a tridentate ligand, M represents a metal selected from Tc and Re, and n is a charge from −2 to +1, provided that $L^3$ is not di-1H-pyrazol-1-ylacetate, bis(3, 5-dimethyl-1H-pyrazol-1-yl)acetate, 1,1,1-methanetriyltris (1H-pyrazole), 1,1,1-methanetriyltris (3,5-dimethyl-1H-pyrazole), 1,4,7-triazacyclononane, 1,4,7-trimethyltriazacyclononane, 1,4,7-trithiacyclononane, hydrotris(1-pyrazolyl)borate or [(η$^5$-C$_5$H$_5$)Co{P(OR)$_2$(=O)}$_3$]$^-$, where R is methyl or ethyl.

In a related aspect of the present invention, there is provided a complex having the formula:

[L$^3$MO$_3$]$^n$ wherein L$^3$ represents a tridentate ligand, M represents a metal selected from Tc and Re, and n is a charge from −2 to +1, wherein L$^3$ represents a tridentate ligand bearing one or more functional groups suitable for facilitating the attachment of a targeting moiety, or bearing one or more linker groups capable of bearing such a functional group, M represents a metal selected from Tc and Re, and n is a charge from −2 to +1, provided that, when L$^3$ bears one or more linker groups, none of which bears a functional group suitable for the attachment of a targeting moiety, at least one of the linker groups contains at least three carbon atoms.

Certain exemplary complexes are depicted in Scheme 1.

Scheme 1. Top left: Basic structure of the [$^{99m}$TcO$_3$]$^+$ core and structures of compounds 1-3 synthesised in the Examples of the present specification.

The present invention is based on a new strategy for making complexes with the [$^{99m}$TcO$_3$]$^+$ or corresponding $^{186}$Re or $^{188}$Re cores accessible for routine radiopharmaceutical purposes. Other isotopes of Tc and Re may, however, be used as necessary. Other isotopes of Tc include 94m, 94, 95m, 96, 97, 97m, 98 and 99 (i.e. ground state). The present invention is somewhat related to the principles behind the chemistry of the corresponding known tricarbonyl precursors [$^{99m}$Tc(CO)$_3$]$^+$ and [Re(CO)$_3$]$^+$, with the exception that the new core is substantially smaller and also much less lipophilic. This alteration in physicochemical properties potentially opens up new applications for complexes containing the new core. In addition, the complexes of the present invention may exert redox activity which might allow further potential uses, for example in hypoxia detection or for the labeling of targeting molecules. The complexes of the invention are of relatively low molecular weight. Compared to the prior art complexes described above, certain complexes of the present invention also have the advantage that they contain functional groups which are available for reaction with an appropriate group on a targeting moiety (or a group capable of modifying the physicochemical properties of the complex, as outlined above) and which thereby allow the complexes to be targeted to particular cells, tissues etc. in vivo. Alternatively, or in addition, certain complexes of the invention contain linker groups which facilitate the incorporation of such functional groups into the complex. The functional groups for facilitating attachment of targeting moieties are preferably spaced away from the rest of the complex, so as to avoid interference with their targeting properties. Accordingly, certain complexes of the present invention preferably contain linker groups having at least three carbon atoms.

The new strategy disclosed herein for making complexes with the [$^{99m}$TcO$_3$]$^+$ and [ReO$_3$]$^+$ cores make these cores accessible for routine radiopharmaceutical purposes.

In particular embodiments of the complexes of the present invention, the Tc is $^{99m}$Tc. When Re is used, the Re may, in particular embodiments, be $^{186}$Re or $^{188}$Re.

In certain embodiments, the one or more functional groups suitable for facilitating the attachment of a targeting moiety are joined to L$^3$ by means of a linker group. As mentioned above, the combination of a functional group suitable for facilitating the attachment or conjugation of a targeting moiety, with a linker group interposed between the functional group and L$^3$, avoids interference with the targeting properties of the targeting moiety.

L$^3$ represents a broad variety of neutral or anionic ligands (with a corresponding variation in the overall charge of the complex), provided that their complexes with Tc(VII) or Re(VII) are water-stable. Suitable ligands L$^3$ are described above in connection with the first aspect of the invention. Stability of the complexes in water is readily determinable by the skilled person, e.g. by means of LC-based analysis of the complexes. Stability of complexes based on a number of ligands, including triazacyclononanes (tacn) and some trispyrazolylmethane based systems, has been confirmed by the present inventors. Complexes containing the corresponding imidazole based ligands also exhibit stability. Complexes prepared according to the present invention have also been confirmed to exhibit stability in the presence of serum proteins.

Due to variations which can be introduced through the ligand L$^3$, a wide variety of complexes can be produced. These may, for example, be useful as perfusion agents, e.g. for diagnosis of myocardial dysfunctions or hypoxia detection. Alternatively or in addition, the ligand L$^3$ can be conjugated to one or more targeting moieties.

In exemplary embodiments of the present invention, L$^3$ is a triazacyclononane, a triaminocyclohexane, a trispyrazolylmethane, a bispyrazolylacetate, a trispyrazolylborate or a corresponding imidazolyl species. In pyrazole or imidazole-containing ligands, the pyrazole or imidazole groups represent the coordinating groups and can bear further functionalities. In embodiments such as these in which L$^3$ contains one or more nitrogen atoms, L$^3$ may be N-substituted with the one or more functional groups suitable for facilitating the attachment of a targeting moiety, or may be N-substituted with the one or more linker groups capable of bearing such a functional group. Alternatively or in addition, L³ may be substituted, e.g. N-substituted, with one or more essentially non-reactive groups which are nevertheless capable of modifying the pharmacological behaviour of the complex. Such groups include short (e.g. $C_1$ or $C_2$) alkyl substituents, or aryl substituents containing no further functional groups.

Suitable linker groups, such as L³ N-substituted linker groups, may be selected from alkyl, alkenyl, aryl, heteroaryl, cycloalkyl, heterocycloalkyl, aralkyl and alkaryl groups, any of which linker groups may be further substituted with a functional group suitable for facilitating the attachment of a targeting moiety. Suitable linker groups are described in more detail above. It will be understood that such groups are also suitable as the above-mentioned essentially non-reactive groups which are nevertheless capable of modifying the pharmacological behaviour of the complex. Thus, in certain embodiments, such linker groups may act merely as substituents on L³, rather than to link a functional group thereto.

The functional group suitable for facilitating the attachment of a targeting moiety (or a moiety suitable for altering the physicochemical properties of the complex) may be selected from hydroxyl, carboxyl, amino, amido, halogen, sulphonyl, alkylsulphonyl, arylsulphonyl, alkylsulphonylamido, arylsulphonylamido, thio, alkylthio, arylthio, phosphonyl, phosphate and cyano. In certain embodiments, the functional group is suitable for reacting with a nucleophilic group on the targeting moiety. In other embodiments, the functional group is suitable for reacting with an electrophilic group on the targeting moiety.

The term 'targeting moiety' as used herein denotes any group which is capable of selective binding to a biological target, such as a receptor or enzyme. Many such moieties are well known to the person skilled in the art, and include biomolecules (which may be selected from, for example, polypeptides, peptides, amino acids, sugars, polysaccharides, nucleosides, nucleotides, oligo- and polynucleotides, growth factors, hormones, antibodies, antibody fragments, endogenous neurotransmitters, and vitamins) and synthetic or semi-synthetic agents which are ligands for the biological target. The skilled person would, furthermore, be readily able to determine whether a given compound was capable of selective binding to a biological target (e.g. using biosensor techniques or radioligand binding studies), and thus capable of acting as a targeting moiety within the context of the present invention.

In particular embodiments of the method of synthesis and the complex of the present invention, at least one linker group on L³, such as a linker group attached as an N-substituent, may comprise a benzyl moiety or a phenyl moiety. A benzyl linker group may be preferred in certain embodiments. Such a benzyl or phenyl moiety may be substituted, for example, with a carboxyl group as a functional group suitable for facilitating the attachment of a targeting moiety. The said functional group is preferably present as a ring substituent in such instances. Such a ring substituent may be present at the para position relative to the position of attachment of the ring to the remainder of the linker group or to L³.

In certain complexes of the present invention, the ligand L³ is modified by conjugation to one or more targeting moieties (or moieties capable of modifying the physicochemical properties of the complex) by means of the functional group(s) suitable for facilitating the attachment thereof.

Such a targeting moiety may be selected from those described above.

In preferred embodiments of the complex of the present invention, the Tc is Tc. As mentioned above, ⁹⁹ᵐTc is the form of Tc of most usefulness in the nuclear medicine field. In such a setting, ⁹⁹ᵐTc is typically obtained in the form of [⁹⁹ᵐTcO₄]⁻ (the pertechnetate ion) in the eluate of a technetium generator. The present invention allows the direct use of pertechnetate for synthesis of complexes containing the [TcO₃]⁺ core directly from saline and without the use of harsh reagents or harsh oxidative or reductive conditions. Accordingly, the present invention makes this core available for routine use in nuclear medicine applications. The same considerations apply to complexes of the invention containing [ReO₃]⁺ cores.

In accordance with a further aspect of the present invention, there is provided a complex having the formula:

[L³MO₃]ⁿ wherein L³ represents a tridentate ligand, M represents a metal selected from Tc and Re, and n is a charge from −2 to +1, provided that L³ is not 1,4,7-triazacyclononane, 1,4,7-trimethyltriazacyclononane, 1,4,7-trithiacyclononane, hydrotris(1-pyrazolyl)borate or [(η⁵-C₅H₅)Co{P(OR)₂(=O)}₃]⁻, where R is methyl or ethyl.

In accordance with another aspect of the present invention, there is provided a pharmaceutical composition comprising a complex as described above, together with one or more pharmaceutically acceptable excipients.

Pharmaceutical compositions of this invention comprise any of the complexes of the present invention, or pharmaceutically acceptable salts and esters thereof, with any pharmaceutically acceptable carrier, adjuvant or vehicle. The pharmaceutical composition of the present invention may take a variety of forms. However, in general, it will be in a form suitable for parenteral administration, e.g. by intravenous, intraarterial (e.g. into the coronary circulation, or the pulmonary artery), intracardiac, intracerebroventricular or intraarteriolar injection. Accordingly, the composition may be in the form of a solution of the complex, such as an aqueous solution of the complex. The pharmaceutical compositions may be in the form of a sterile injectable preparation, for example, a sterile injectable solution or suspension in a non-toxic parenterally-acceptable diluent or solvent. Among the acceptable vehicles and solvents that may be employed are mannitol solution, water, Ringer's solution and isotonic sodium chloride solution (i.e. normal saline). If necessary, additional excipients to enhance the solubility of the complexes may be added, for example, non-ionic surfactants (e.g. those selected from the Span or Tween groups of compounds) or polyalkylene glycols.

When the pharmaceutical composition of the invention is in the form of a solution, the pH of the solution may be from about 5 to about 9, in particular from about 6 to about 8. The complexes of the invention have been found to be stable over a wide range of pH values. Importantly, they have been found to be particularly stable in the range of pH of most relevance to use in nuclear medicine (i.e. 5 to 9). For an illustration of such stability, reference may be made to FIG. 6 herein.

In accordance with a further aspect of the invention, there is provided a method of purifying a complex having the formula:

[L³MO₃]ⁿ wherein L³ represents a tridentate ligand, M represents a metal selected from Tc and Re, and n is a charge from −2 to +1, the method comprising contacting a non-purified solution of complex with an inorganic or organic polymeric substrate bearing functional groups capable of reacting with [L³TcO₃]ⁿ or [L³ReO₃]ⁿ, followed by washing of the polymeric substrate to remove unbound material.

Complexes according to the present invention are capable of reacting with appropriately functionalised inorganic or organic polymers. The functional groups borne by the polymeric substrate may, in particular embodiments, be capable of acting as reducing agents or Lewis acids in reaction with [L³MO₃]ⁿ. For example, the complexes will react with phosphine-functionalised inorganic or organic polymers. After such a reaction, all other material can be washed away from the solid phase-bound complex. The complex may then be cleaved from the polymer using a mild oxidant, such as aerated water. In the case of complexes containing the preferred isotope, $^{99m}$Tc, the complexes are bound to the inorganic or organic polymer and non-radioactive material is then washed away from the bound complex. Subsequent cleavage with aerated water or another mild oxidant is thus capable of giving no-carrier-added radiopharmaceuticals.

The invention also provides, in yet another aspect, a method of synthesising a diolato derivative of $[L^3MO_3]^n$, the method comprising the reaction of a composition according to the second aspect of the invention as described above, or a complex according to the third aspect as described above, with an alkene, alkyne or an alkenyl or alkynyl group-containing species, wherein $L^3$, M and n have the same meanings as defined above in relation to the first aspect.

Macroscopic weighable amounts of complexes $[L^3MO_3]^+$ with ground state Tc-99 react in organic solvent (or aqueous media) with alkenes to receive the corresponding water stable diolato derivatives. This reaction represents a type of "click" chemistry (a [2+3] cyclo-addition). This reaction leads to the possibility for direct labeling of targeting moieties and biomolecules possessing either endogenous alkenes (for example, unsaturated fatty acids) or having coupled alkenes or alkynes of any sort. In particular embodiments of this method, the alkenyl or alkynyl group forms part of, or is coupled to, a targeting moiety. As with the other aspects of the present invention, the preferred isotope of Tc is $^{99m}$Tc and that of Re is $^{186}$Re or $^{188}$Re. The diolato derivatives resulting from the reaction are highly stable in water. Furthermore, when the alkenyl or alkynyl group is attached to or present as part of a targeting moiety, the resulting diolato derivatives may be used for targeting $^{99m}$Tc to particular organs or tissues for diagnostic and/or imaging purposes. An exemplary reaction is shown in Scheme 2.

Scheme 2: Illustrative reaction of a complex of the invention with an alkenyl group-containing species In a related aspect, the invention also provides a diolato derivative of $[L^3MO_3]^n$, having the formula $[L^3MO(OC(R1R2)C(R3R4)O)]^n$ or $[L^3MO(OC(R1)=C(R2)O)]^n$, wherein M, $L^3$ and n have the same meaning as defined above in relation to the third aspect of the invention, wherein the proviso to the third aspect applies, and wherein R1, R2, R3 and R4 are independently selected from H, a targeting moiety, a functional group attached to, or suitable for facilitating the attachment of, a targeting moiety, and a linker group bearing, or capable of bearing, such a functional group.

In particular embodiments of this aspect of the invention, R1, R2, R3 and/or R4 is a targeting moiety, which may be joined to the complex via a linker group, a functional group suitable for facilitating the attachment of the targeting moiety, or a combination thereof. Thus, it will be understood that the targeting moiety may be joined to the complex via a functional group R1, R2, R3 or R4, or may be joined via a functional group at the end of a linker group R1, R2, R3 or R4. Alternatively, where the alkenyl group forms part of a targeting moiety (such as an endogenous biomolecule), it will be understood that R1, R2, R3 and/or R4 will comprise all or part of that targeting moiety. The advantages of complexes bearing targeting moieties, particularly in relation to $^{99m}$Tc, are outlined above.

In another related aspect, the invention also provides a composition comprising an aqueous solution of a diolato derivative of $[L^3MO_3]^n$ having the formula $[L^3MO(OC(R1R2)C(R3R4)]^n$ or $[L^3MO(OC(R1)=C(R2)O)]^n$, wherein M, $L^3$ and n have the same meaning as defined above in relation to the first aspect of the invention, wherein R1, R2, R3 and R4 are independently selected from H, a targeting moiety, a functional group attached to, or suitable for facilitating the attachment of, a targeting moiety, and a linker group bearing, or capable of bearing, such a functional group, and wherein the composition is obtained or obtainable by the method of synthesising a diolato derivative described above, wherein the said method is carried out in an aqueous medium.

The composition comprising an aqueous solution of a diolato derivative may, in certain embodiments, comprise a complex in which $L^3$ is not 1,4,7-triazacyclononane.

The present invention also provides a complex or a composition according to the invention as described above, for use in therapy or diagnosis.

The present invention also provides a complex or a composition according to the invention as described above, for use in the diagnosis and/or imaging of disorders of organ haemoperfusion and/or hypoxic states, or the measurement and/or imaging of tumor haemoperfusion and/or hypoxia.

In a similar aspect, the present invention also provides the use of a complex or a composition according to the invention as described above in the preparation of a medicament for the diagnosis and/or imaging of disorders of organ haemoperfusion and/or hypoxic states, or the measurement and/or imaging of tumor haemoperfusion and/or hypoxia.

Furthermore, the present invention also provides, in a related aspect, a method of diagnosis of disorders of organ haemoperfusion and/or hypoxic states, or measurement and/or imaging of tumor haemoperfusion and/or hypoxia, in a subject, the method comprising the administration to the subject of a complex or a composition according to the invention as described above.

In certain embodiments of this method, the method further comprises the acquisition of data related to the location of the complex within the subject following administration. Moreover, the method may further comprise the generation of an image based on the acquired data.

In a further related aspect, the present invention also provides a method of imaging organ haemoperfusion and/or hypoxic states, or tumor haemoperfusion and/or hypoxia, in a subject, the method comprising the steps of: administration to the subject of a complex or a composition according to the invention as described above, the acquisition of data related to the location of the complex within the subject following administration; and generation of an image based on the acquired data.

In the diagnostic, imaging and/or therapeutic uses of the complexes of the invention described herein, the organ whose haemoperfusion is under consideration may, in particular embodiments, be selected from the heart and the lungs.

The invention will now be described in more detail by way of example only and with reference to the appended drawings, of which:

FIGS. 1(a) and 1(b) show analytical (HPLC) results for a complex produced by the method of the present invention (Compound 1) (Reaction of $[TcO_4]^-$+triazacyclononane.3HCl+PPh$_3$ (loaded polymer)) under two conditions of mobile phase in order to distinguish between pertechnetate and the complexes of the invention, with detection by γ radioactivity (Compound 1 containing $^{99m}$Tc) and UV absorption (corresponding complex containing ground state $^{99}$Tc). FIG. 1(a) relates to use of the mobile phase TEAP/MeCN (due to the experimental setup the γ-signal has a 0.56 min delay compared to the uv-signal), whereas FIG. 1(b) relates to use the mobile phase TFA/MeCN (γ-signal has a 0.54 min delay compared to the uv-signal);

FIG. 7 shows (a) the γ-trace of the diolato derivative Compound 4 (TEAP/MeCN), prepared by the reaction of [TcO$_3$(tacn)]$^+$+StyreneSO$_3$Na, 1.5 h at 95° C., and (b) the β-trace of the same;

The present inventors have developed a synthetic method to prepare complexes of the general composition $[L^3TcO_3]^+$ (where $L^3$ is as defined above (for exemplary embodiments of $L^3$, see scheme 1)) directly from water (saline). Whereas some Tc(VII) complexes have been described in the prior art for ground state $^{99}$Tc, none of these has been prepared with $^{99m}$Tc or from an aqueous medium. The reaction conditions for the ground state $^{99}$Tc complexes of the prior art are very rough and include concentrated nitric or sulfuric acid or 30% peroxide solutions, conditions not suitable for adaptation to routine requirements coming from nuclear medicine applications.

Compound 1 is known for ground state $^{99}$Tc, compounds 2 and 3 have not previously been described, and 3 in particular possesses a carboxylate function which can readily be conjugated to targeting moieties, such as biomolecules. None of these compounds is known from the prior art for $^{99m}$Tc. Compounds 1-3 (scheme 1) have now been synthesised directly from generator eluate, according to the method outlined below.

Synthetic Approach

The two different pathways which have been employed for the preparation of complexes of the present invention are as follows: i) pertechnetate is activated by formation of an ester or a similar structural unit with a Lewis acid (usually a strong Lewis acid, i.e. such that the pertechnetate acts as a Lewis base and reaction takes place at an oxygen atom of pertechnetate) before ligand substitution takes place; or ii) reduction to Tc(V) and coordination of the ligand, with subsequent oxidation by air. It is believed that coordination takes place essentially concomitantly upon reduction, although the inventors do not wish to be bound by this belief. The same procedures (i) and (ii) may be employed with perrhenate.

Organic or inorganic polymer bound phosphine may, optionally, be used for both pathways (see Scheme 2 below). Illustrative reactions of phosphines with technetium-containing species, and their use as reducing agents, are described in US 20040042963 and Greenland and Blower (*Bioconjugate Chem.*, 2005, 16, 939-48), respectively.

In brief, generator eluate is mixed with the inorganic or organic polymer in the presence of ligand $L^3$. Heating provides the desired complexes 1-3 with the $[^{99m}TcO_3]^+$ core. The compounds are received in good radiochemical purity. The advantage of this synthetic approach is the fact that no other substances are required with the exception of $[^{99m}TcO_4]^-$ and the ligand $L^3$. Thus, no additional reducing agents, solvents or auxiliary ligands are needed, unlike in the prior art. Although the inventors do not wish to be bound by any particular theory as to the precise mechanistic details, the results imply that $[^{99m}TcO_4]^-$ might react with the inorganic or organic polymer but does not bind to it persistently in the absence of ligands $L^3$.

Scheme 3: Preparation of compounds [L3TcO₃]⁺ with polymer bound phosphines via the redox pathway (A) or by activation with a non-redox Lewis acid (B)

-continued

Tc(V)

Figure 4:
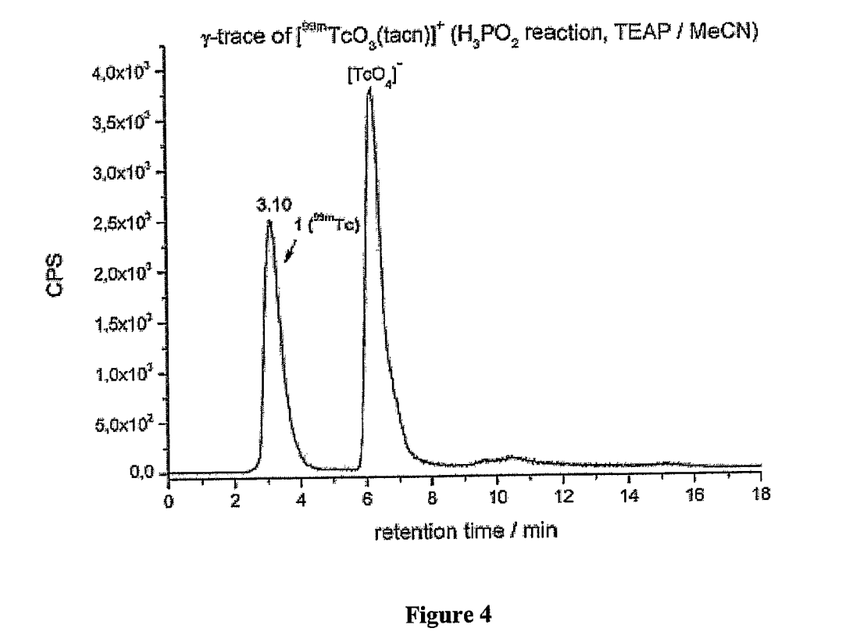
FIG. 4 shows the γ-trace of Compound 1 (TEAP/MeCN) prepared by homogeneous reaction of $[TcO_4]^-$+triazacyclononane.3HCl+H$_3$PO$_2$.
Figure 5:
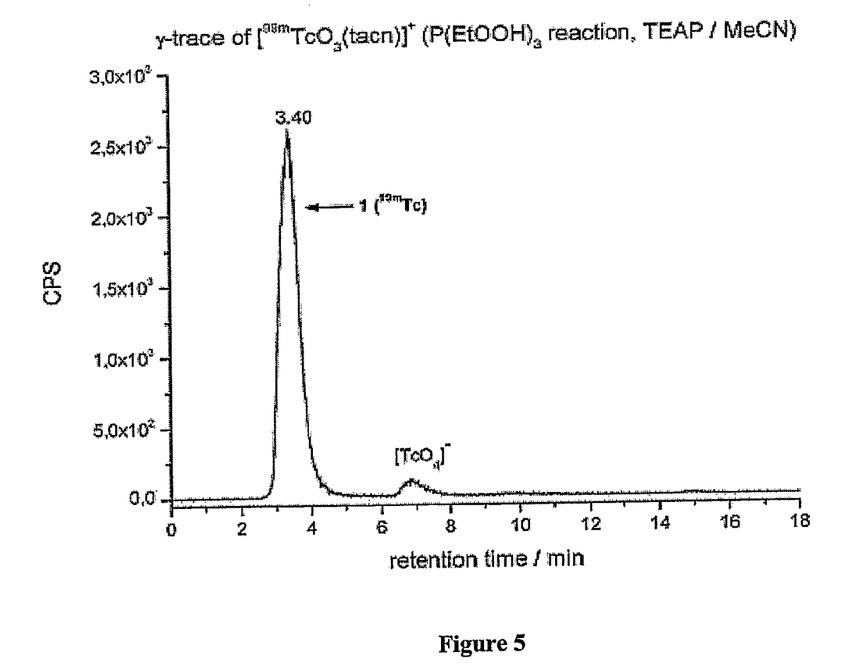
FIG. 5 shows the γ-trace of Compound 1 (TEAP/MeCN) prepared by reaction of $[TcO_4]^-$+triazacyclononane.3HCl+P(EtOOH)$_3$ (loaded polymer)

It will be appreciated by the skilled person that the syntheses of the present invention may equally be carried out by a homogeneous reaction, i.e. using reducing agent or activating Lewis acid in aqueous solution (FIG. 4).

EXAMPLE 1

Illustrative details of both homogeneous and heterogeneous syntheses, using pertechnetate as an example, are as follows:

1.1 Polymer-Bound Phosphine

Kit 1:
- 10 mg polymer bound triphenylphospine (200-400 mesh, extent of labeling: ~3.0 mmol/g loading, 2% cross-linked with divinylbenzene, Aldrich)
- 23.5 mg ($10^{-4}$ mol) 1,4,7-Triazacyclononane trihydrochloride
- 2.81 μl $H_2SO_4$ Protocol 1:
The prepared kit 1 was flushed with $N_2$ for 10 min. 1 ml of eluted $[TcO_4]^-$ solution was added and the reaction mixture was heated for 4 h at 95° C. The reaction solution was filtered and neutralized by the addition of NaOH (0.1M).
Yield: 48%

Kit 2:
- 10 mg polymer bound tris(2-carboxy-ethyl)phosphine hydrochloride (NovaSyn® amino resin (90 μm), extent of labeling: ~0.3 mmol/g, loaded by standard SPPS technique, resin is a composite of polyethylene glycol and a low-cross linked polystyrene gel-type resin, good swelling properties in water, Novabiochem)
- 23.5 mg ($10^{-4}$ mol) 1,4,7-Triazacyclononane trihydrochloride Protocol 2:
The prepared kit 2 was flushed with $N_2$ for 10 min. 1 ml of eluted $[TcO_4]^-$ solution was added and the reaction mixture was heated for 1 h at 95° C. The reaction solution was filtered and neutralized by the addition of NaOH (0.1M).
Yield: 70%

1.2 Phosphinic Acid (i.e. Homogeneous Synthesis)

Kit:
- 0.62 μl 50% (5.7 $10^{-5}$ mol) Phosphinic acid (Fluka)
- 23.5 mg ($10^{-4}$ mol) 1,4,7-Triazacyclononane trihydrochloride
- 2.81 μl $H_2SO_4$

Protocol
The prepared kit was flushed with $N_2$ for 10 min. 1 ml of eluted $[TcO_4]^-$ solution was added and the reaction mixture was heated for 4 h at 95° C. After 2 h the vial was opened and air was allowed to enter the reaction vessel. The reaction solution was neutralized by the addition of NaOH (0.1M).
Yield: 64%

It was found that there was no necessity to allow additional air into the heterogeneous reaction vessel following the coordination step. It is believed that there was already sufficient air in the vial to provide for the final oxidation/cleavage step.

It will be appreciated by the skilled person that the heterogeneous reaction could be carried out in a kit in the form of a column packed with the inorganic or organic polymeric phosphine (or other reducing agent/activating Lewis Acid), into which the generator eluate and $L^3$ are introduced in solution.

1.3 Borane Adducts of Amines (i.e. Homogeneous Synthesis)

Figure 10:
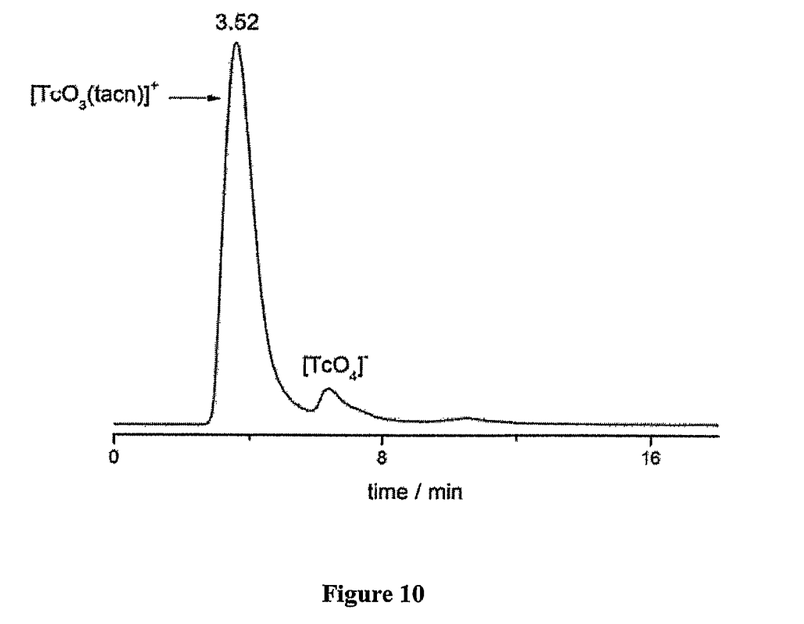
FIG. 10 shows the γ-trace of Compound 1 prepared by homogeneous reaction of $[TcO_4]^-$ and an adduct of triazacyclononane and borane.

Kit: 14.3 mg $H_3B(tacn)$ ($10^{-4}$ mol), having the following structure:

Protocol: The kit containing $H_3B(tacn)$ was flushed with $N_2$ for 10 min. 1 ml of eluted $[TcO_4]^-$ solution was added and the reaction mixture was heated for 15 min at 95° C.
Yield: 96%. The HPLC trace for the product is shown in FIG. 10.

1.4 Reaction of Pertechnetate with an Amino-Phosphoylid of tacn

Kit: 10 mg $(Ph_3P(tacn))Br$ ($2 \cdot 10^{-5}$ mol), having the following structure:

$$\left[ \begin{array}{c} Ph \\ Ph-P^{\oplus}-N \\ Ph \end{array} \begin{array}{c} H \\ N \\ N \\ H \end{array} \right] Br$$

Figure 11:
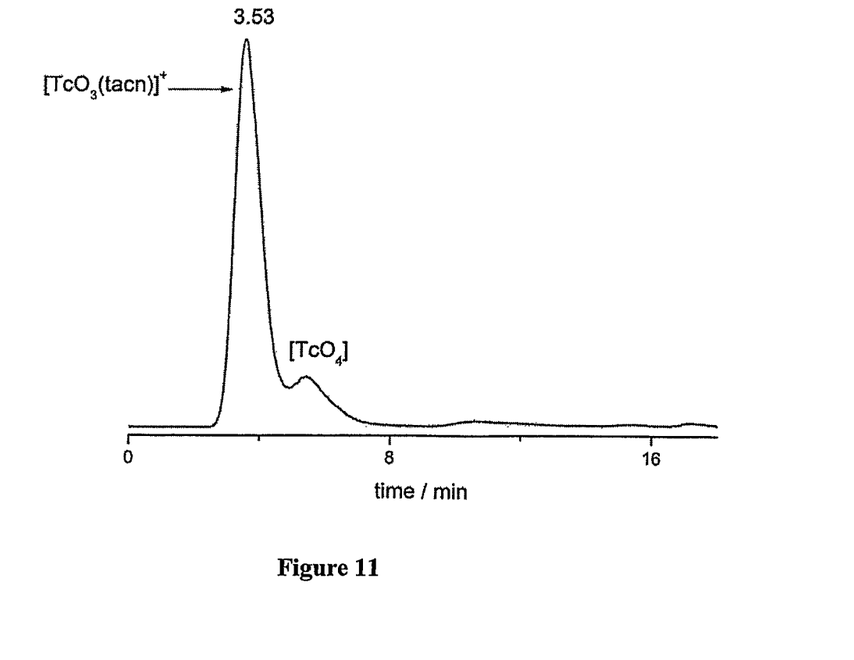
FIG. 11 shows the γ-trace of Compound 1 prepared by homogeneous reaction of $[TcO_4]^-$ and an adduct of triazacyclononane and triphenylphosphine.

Protocol: The kit containing $(Ph_3P(tacn))Br$ was flushed with $N_2$ for 10 min. 1 ml of eluted $[TcO_4]^-$ solution was added and the reaction mixture was heated for 6 h at 95° C.
Yield: 95%. The HPLC trace for the product is shown in FIG. 11.

1.5 Use of $Na[BH_4]$ as Reducing Agent

Kit:
- 2.4 mg 1,4,7-Triazacyclononane trihydrochloride ($10^{-5}$ mol)
- 2.6 mg $NaBH_4$ ($6.9 \cdot 10^{-5}$ mol)
- 5.6 mg NaOH ($1.4 \cdot 10^4$ mol)

Figure 12:
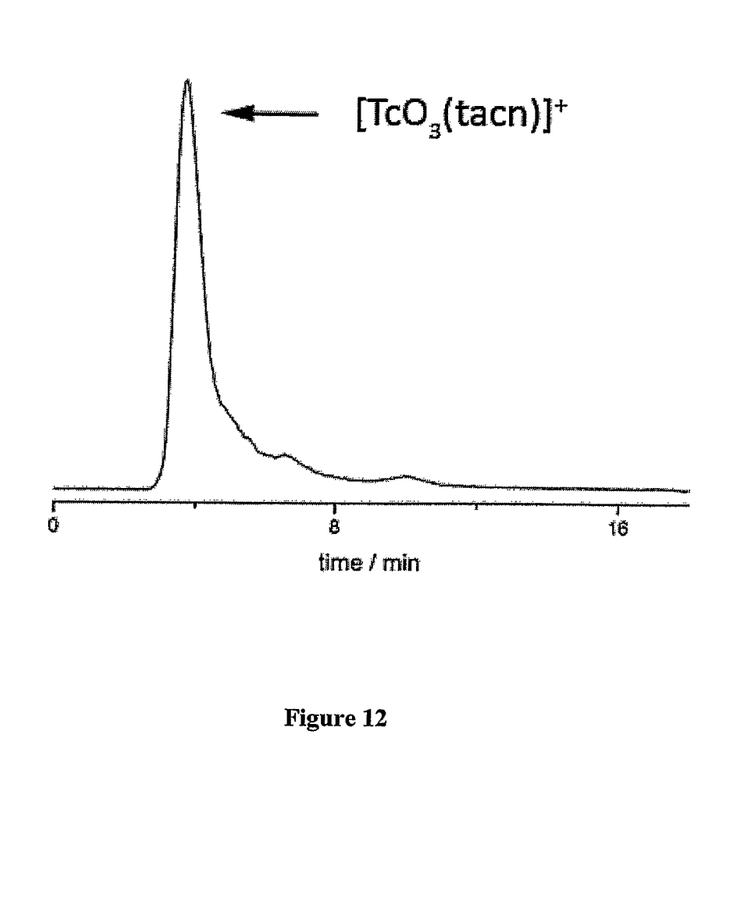
FIG. 12 shows the γ-trace of Compound 1 prepared by homogeneous reaction of $[TcO_4]^-$, triazacyclononane and sodium borohydride.

Protocol: The prepared kit was flushed with $N_2$ for 10 min. 1 ml of eluted $[TcO_4]^-$ solution was added and stirred for 15 min at room temperature. The reaction mixture was neutralized by the addition of HCl (0.1M).
Yield: 97%. The HPLC trace for the product is shown in FIG. 12

EXAMPLE 2

A diolato derivative of the present invention may be prepared as follows:
Compound 4 (Reaction of Compound 1 with 4-Vinylbenzenesulfonic Acid Sodium Salt):

Compound 1 was prepared following the heterogeneous method by using the polymer-bound tris(2-carboxy-ethyl) phosphine hydrochloride as reducing reagent. 3.2 mg ($1.55 \times 10^{-5}$ mol) 4-Vinylbenzenesulfonic acid sodium salt hydrate was added to the filtered and neutralized solution (0.8 ml). The reaction mixture was heated to 95° C. for 1.5 h.

Yield: 78%

EXAMPLE 3

Stability

Figure 8:
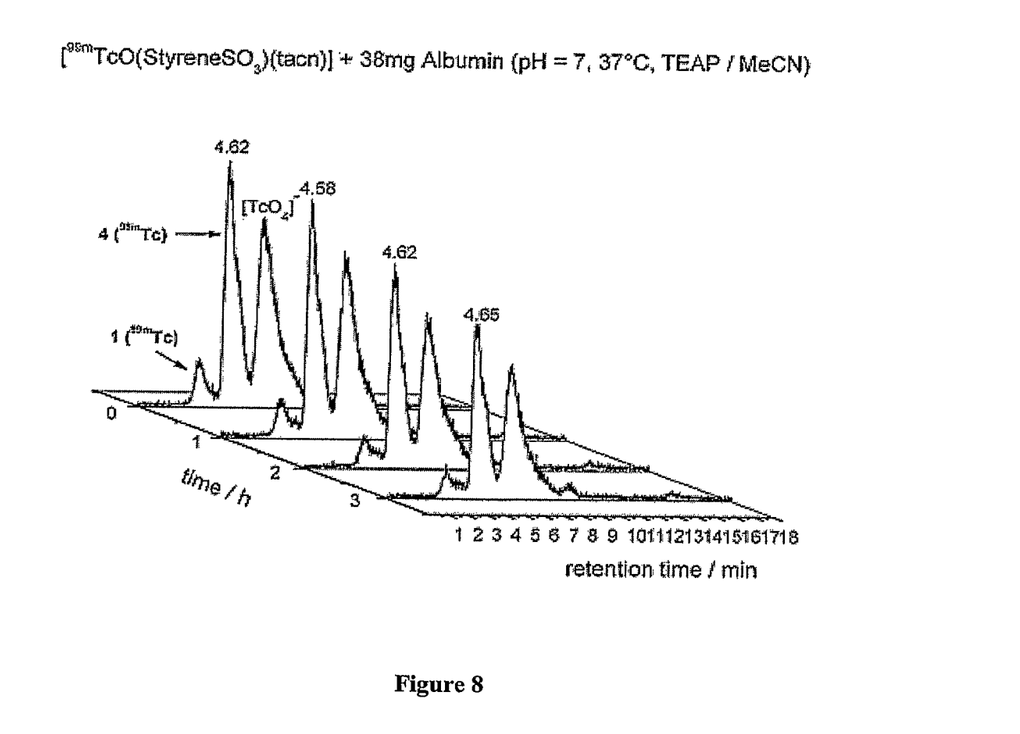
FIG. 8 illustrates stability studies of Compound 4 in the presence of Albumin (TEAP/MeCN)

Stability Studies with Albumin:

38 mg of Albumin from bovine serum (solubility: 40 mg/ml) were added to a solution (1 ml) of compound 4. No decomposition of compound 4 was observed over 3 h at 37° C. (FIG. 8)

Figure 9:
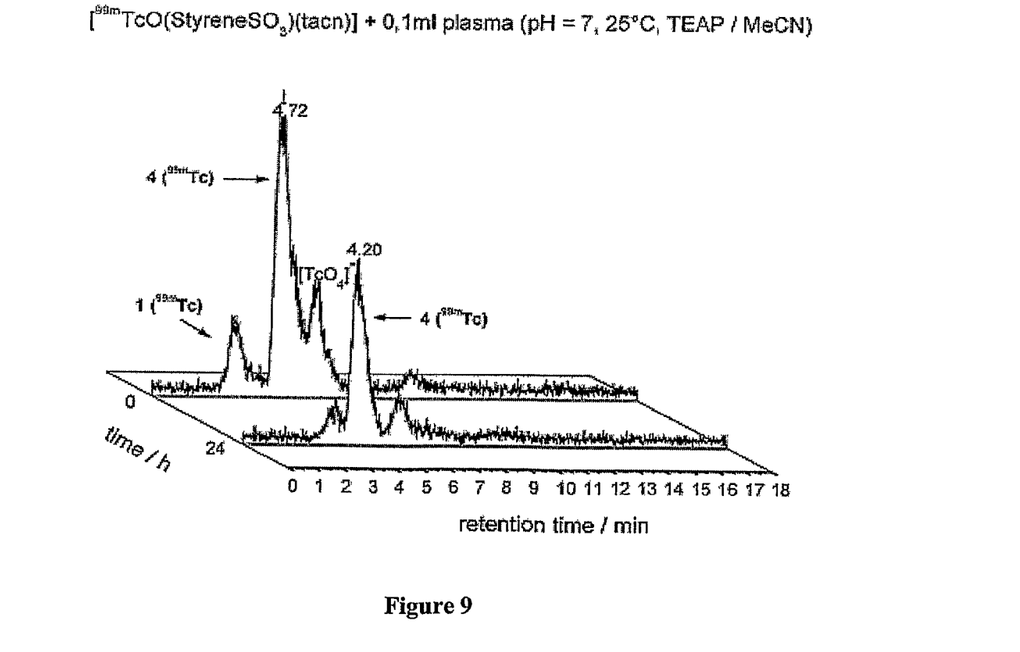
FIG. 9 illustrates stability studies of Compound 4 in the presence of plasma (TEAP/MeCN)

Stability Studies with Plasma:

0.1 ml of plasma (bovine) was added to a solution of Compound 4. No decomposition of compound 4 was observed over 24 h at 25° C. (FIG. 9)

Characterisation of Complexes

Details of the HPLC Conditions

HPLC analyses were performed on a Merck Hitachi LaChrom L 7100 pump coupled to a Merck Hitachi LaChrom L7200 tunable UV detector and a radiodetector, separated by a Teflon tube which causes about a 0.5 min delay compared to Uv/vis detection. Uv/vis detection was performed at 250 nm. The detection of radioactive $^{99m}$Tc complexes was performed with a Berthold LB506 radiodetector equipped with a NaI(Tl) scintillation detector. Due to detector setup the $^{99m}$Tc signals appear generally 0.4-0.7 min later compared to the UV signal of the corresponding $^{99}$Tc complexes. Separations were achieved on a Macherey-Nagel C18 reversed-phase column (Nucleosil 10 lm, 250 4 mm) using a gradient of MeCN/0.1% $CF_3COOH$ or MeCN/50 mM TEAP as eluent, and flow rates of 0.5 mL/min. Method 1 (for compound 1 and 2): t=0-3 min: 0% MeCN; 3-3.1 min: 0-25% MeCN; 3.1-9 min: 25% MeCN; 9-9.1 min: 25-34% MeCN; 9.1-18 min: 34-100% MeCN; 18-25 min: 100% MeCN, 25-25.1 min: 100-0% MeCN; 25.1-30 min: 0% MeCN. Method 2 (for compound 3 and 4): t=0-3 min: 0% MeCN; 3-3.1 min: 0-25% MeCN; 3.1-9 min: 25% MeCN; 9-9.1 min: 25-34% MeCN; 9.1-12 min: 34% MeCN; 12-12.1 min: 34-100% MeCN, 12.1-15 min: 100% MeCN, 15-15.1 min: 100-0% MeCN; 15.1-18 min: 100% MeCN.

Figure 1A:
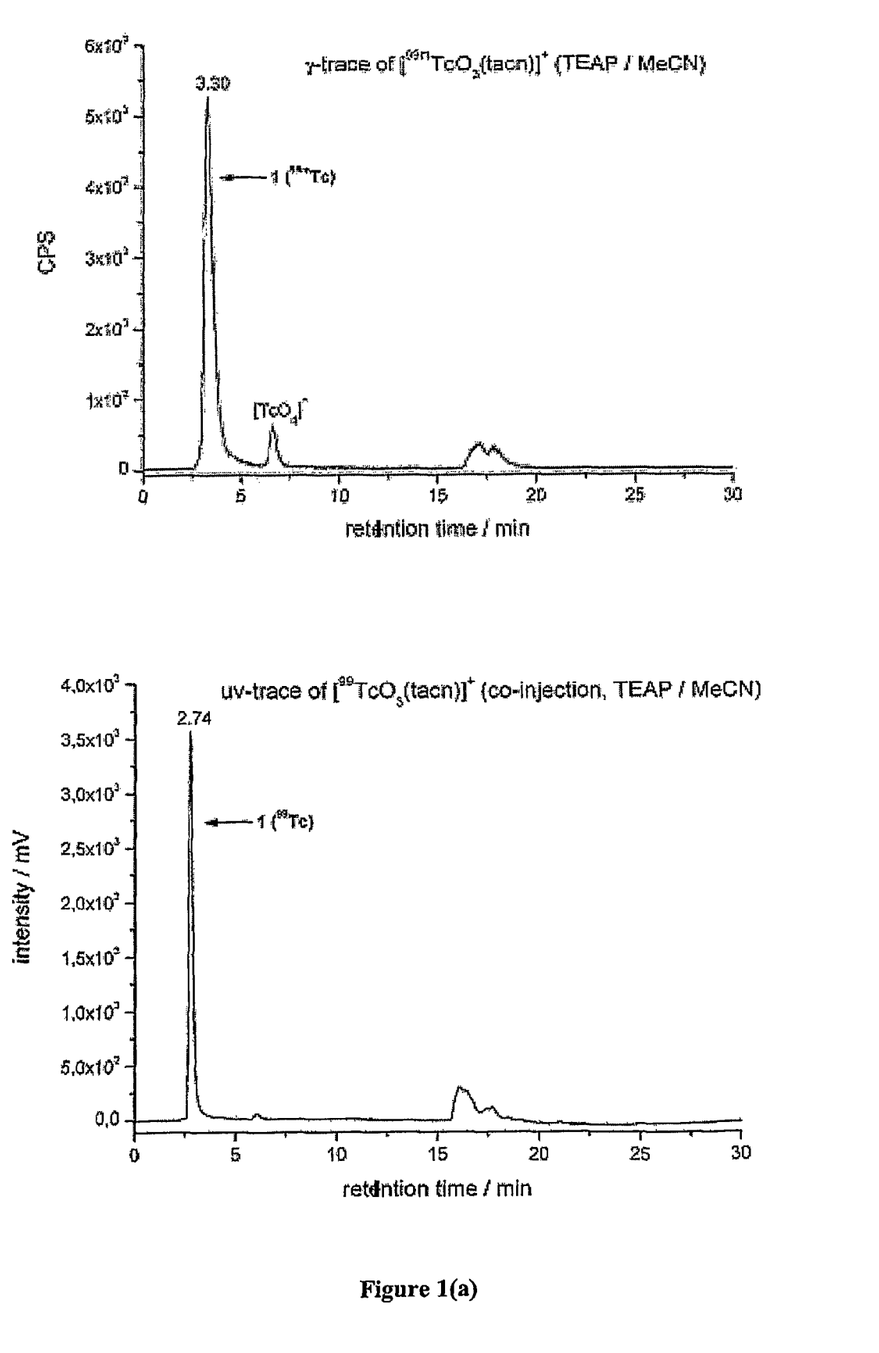
Figure 1B:
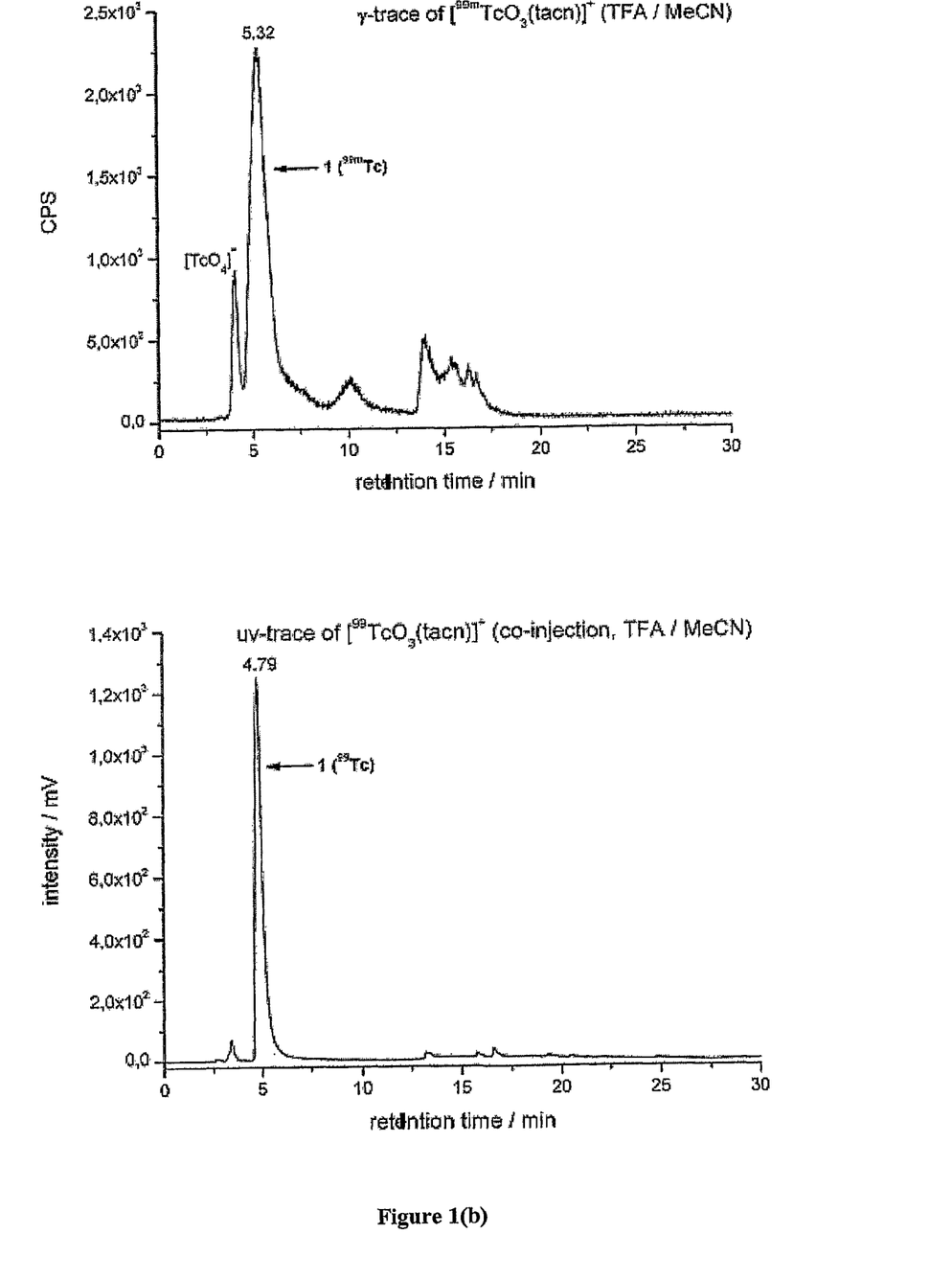
Figure 2:
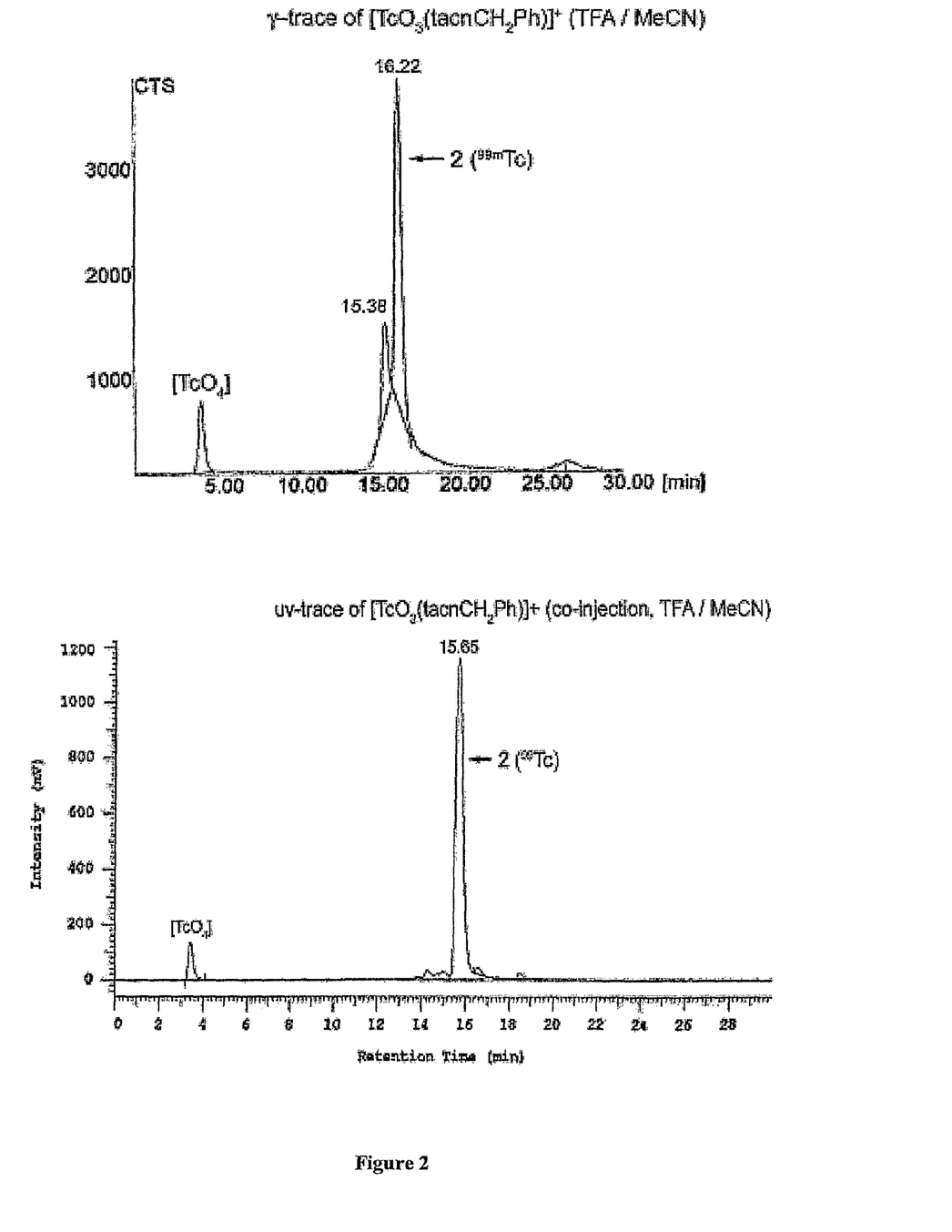
FIG. 2 shows HPLC results for a further complex of the invention (Compound 2) (Reaction of $[TcO_4]^-$+N-benzyl-triazacyclononane+PPh$_3$ (loaded polymer)), with detection by γ radioactivity (Compound 2 containing $^{99m}$Tc), and UV (corresponding complex containing ground state $^{99}$Tc), using the TFA/MeCN mobile phase. Due to the experimental setup the γ-signal has a 0.57 min delay compared to the uv-signal.
Figure 3A:
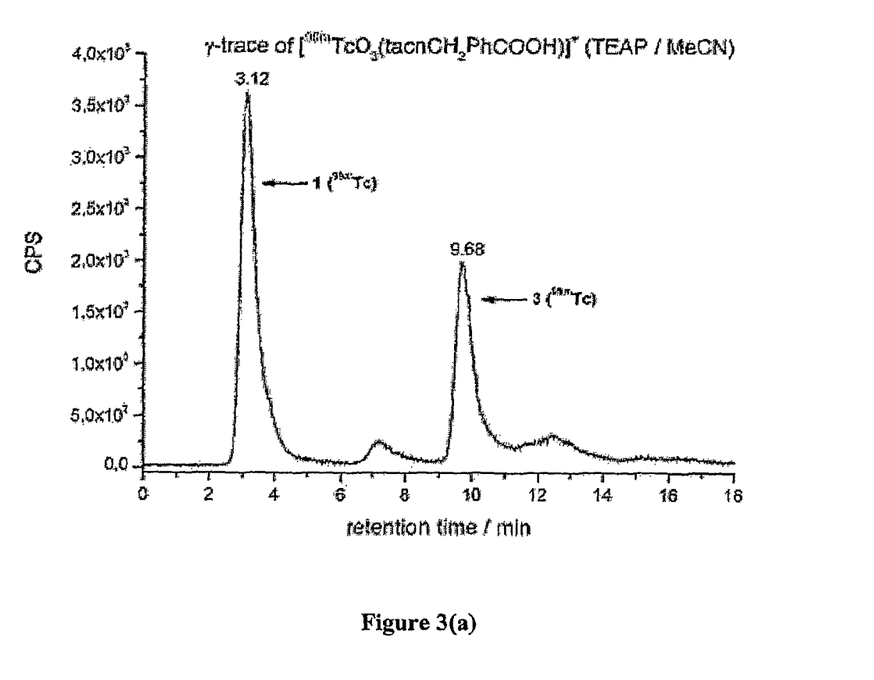
FIG. 3 shows HPLC results for a third complex of the invention (Compound 3) (Reaction of $[TcO_4]^-$+N-(4-carboxy)benzyl-triazacyclononane.3HCl+PPh$_3$ (loaded polymer)), with detection by (a) γ radioactivity (Compound 3 containing $^{99m}$Tc), and (b) β radioactivity (corresponding complex containing ground state $^{99}$Tc), using the TEAP/MeCN mobile phase. Due to different detector systems the β-signal is detected ca. 1.5 min later than the γ-signal.
Figure 3B:
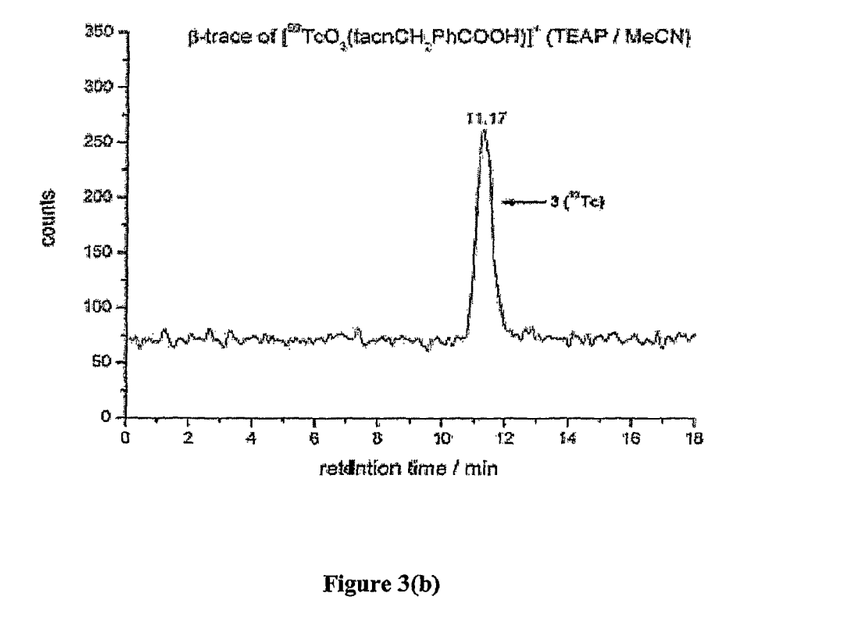

Comparison of the HPLC retention times for the $^{99m}$Tc compounds with the corresponding $^{99}$Tc compounds confirms identity (FIGS. 1 to 3). The comparison for 1 (FIG. 1) is somewhat harder since it elutes practically with the front of the mobile phase at very early times and close to pertechnetate. However, even for 1, the formation is shown by applying different HPLC gradients and solvents. Thus, by employing a tetraethylammonium perchlorate/acetonitrile (TEAP/MeCN) mobile phase (rather than a trifluoracetic acid (TFA)/MeCN mobile phase), the resolution between the complex and pertechnetate was improved. Note that the difference in retention times between the $^{99m}$Tc and $^{99}$Tc based complexes (FIGS. 1a and 1b, in the case of Compound 1) was generally around 0.4. to 0.7 minutes.

The TEAP/MeCN mobile phase was subsequently used for Compounds 2 and 3. Confirmation for Compounds 2 and 3 is unambiguous (FIGS. 2 and 3; note that the peak at 15.38 in FIG. 2 represent artefact from the column). Particularly in relation to Compound 3, the HPLC data (FIG. 3(a)) implies the formation of Compound 1 as well (peak at 3.12 minutes).

Figure 6:
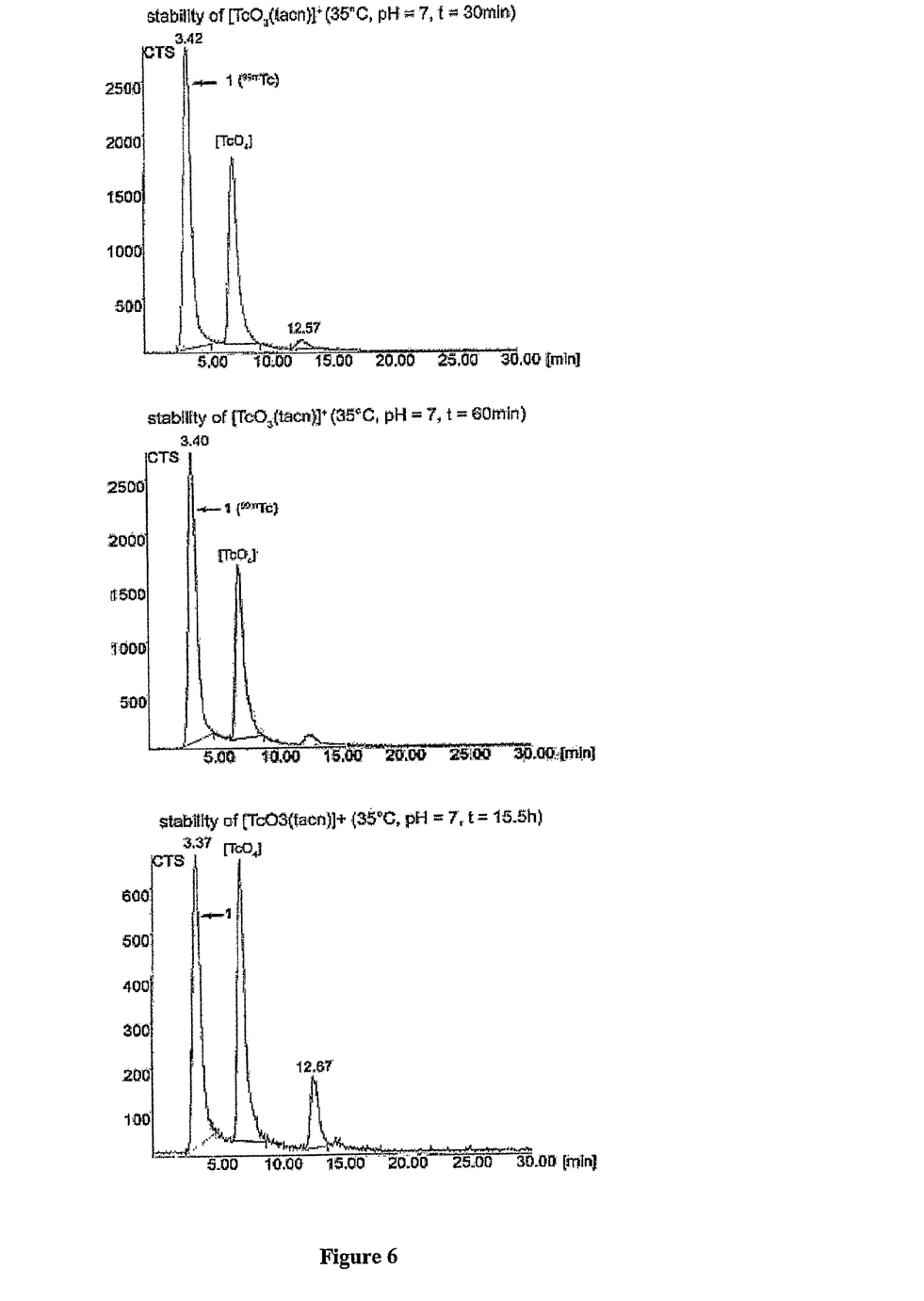
FIG. 6 shows a series of traces to illustrate stability studies of Compound 1 at pH=7 (γ-trace, TEAP/MeCN)
Figure 7A:
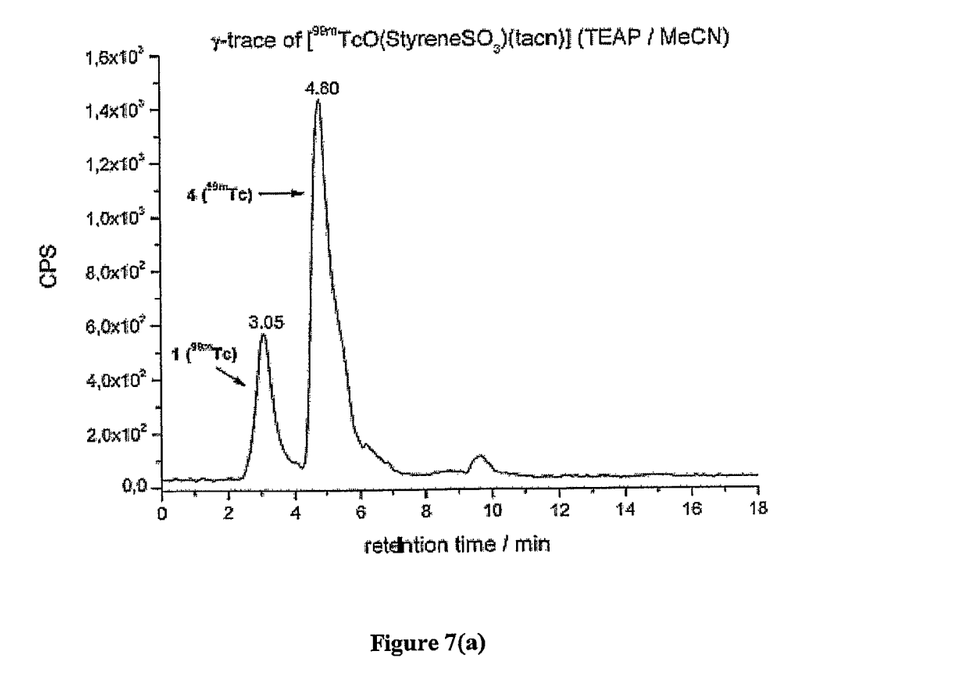
Figure 7B:
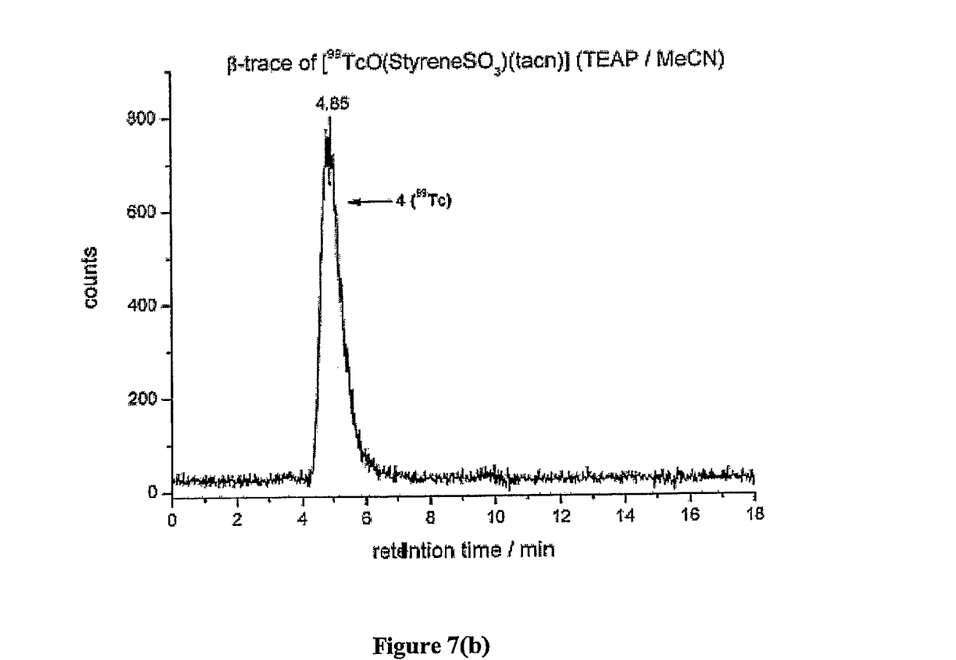

It was found that the compounds 1 to 3 were stable in saline between pH 6 and 8 for hours without any hydrolysis to pertechnetate (e.g. for compound 1 see FIG. 6). Furthermore, model experiments using compound 1 but with $^{99}$Tc showed that the complex can be kept at pH 1 for days without significant hydrolysis.

In conclusion, the preparative route disclosed herein is not suggested by the prior art and allows a much more convenient approach to the preparation of both known and novel desired complexes than those which have previously been described for ground state $^{99}$Tc. The present invention potentially allows a wide variety of new and easily prepared compounds of potential usefulness for radiopharmaceutical applications to be produced. The invention also opens up methods of labeling through reaction of the complexes of the invention with alkenes, alkynes and alkenyl or alkynyl groups, and the straightforward preparation of no carrier added radiopharmaceuticals.

The invention claimed is:

1. A method for synthesizing a complex having the formula:

$$[L^3MO_3]^n$$

wherein $L^3$ represents a tridentate ligand selected from the group consisting of a triazacyclononane, a triaminocyclohexane, a trispyrazolylmethane, a bispyrazolylacetate, a trispyrazolylborate, and a corresponding imidazolyl species, M represents a metal selected from Tc and Re, and n is a charge from −2 to +1, the method comprising:
a) reacting pertechnetate or perrhenate with a reducing agent and $L^3$, or
b) reacting pertechnetate or perrhenate with a Lewis acid and $L^3$,
wherein the synthesis (a) or (b) is carried out in an aqueous medium.

2. The method according to claim 1, wherein the method comprises:
a) i) reacting pertechnetate or perrhenate with a reducing agent; ii) coordinating $L^3$ with the resulting Tc or Re species, respectively; and iii) oxidizing the Tc or Re species to the (VII) oxidation state;
or
b) i) reacting pertechnetate or perrhenate with a Lewis acid; and ii) coordinating $L^3$ with the resulting Tc or Re species.

3. The method according to claim 1, wherein the reducing agent used in (a) is a Lewis base.

4. The method according to claim 3, wherein the reducing agent is a phosphine bound to an inorganic or organic polymer.

5. The method according to claim 1, wherein the reducing agent is selected from phosphites, sulphites, hypophosphites, and hydrides.

6. The method according to claim 1, wherein the reaction is carried out in saline.

7. The method according to claim 1, wherein the tridentate ligand $L^3$ further comprises one or more functional groups suitable for facilitating the attachment of a targeting moiety, or bearing one or more linker groups capable of bearing such a functional group.

8. The method according to claim 1, wherein $L^3$ is N-substituted with one or more functional groups suitable for facilitating the attachment of a targeting moiety, or is N-substituted with one or more linker groups capable of bearing such a functional group.

9. The method according to claim 1, wherein $L^3$ and the reducing agent, or $L^3$ and the Lewis acid, are presented simultaneously in the form of an adduct or conjugated form of these two components.

10. The method according to claim 1, further comprising purifying the complex by contacting a non-purified solution of the complex with an inorganic or organic polymeric substrate bearing functional groups capable of reacting with $[L^3TcO_3]^n$ or $[L^3ReO_3]^n$, followed by washing of the polymeric substrate to remove unbound material.

11. The method according to claim 10, wherein the functional groups borne by the inorganic or organic polymeric substrate are capable of acting as reducing agents or Lewis acids in reaction with $[L^3MO_3]n$.

12. The method according to claim 11, wherein the method further comprises subsequent cleavage of the complex from the inorganic or organic polymeric substrate under oxidizing conditions.

\* \* \* \* \*